US012584090B2

(12) United States Patent
Thiel et al.

(10) Patent No.: US 12,584,090 B2
(45) Date of Patent: Mar. 24, 2026

(54) DEVICE FOR ENSURING A STERILE ENVIRONMENT FOR INCUBATING CELL CULTURES

(71) Applicant: S-BIOSYSTEMS GMBH, Siegen (DE)

(72) Inventors: Erwin Richard Thiel, Siegen (DE);
Christoph Zander, Freudenberg (DE);
Stephan Irle, Siegen (DE)

(73) Assignee: S-BIOSYSTEMS GMBH, Siegen (DE)

( * ) Notice: Subject to any disclaimer, the term of this patent is extended or adjusted under 35 U.S.C. 154(b) by 582 days.

(21) Appl. No.: 18/016,175

(22) PCT Filed: Jul. 14, 2021

(86) PCT No.: PCT/EP2021/069642
§ 371 (c)(1),
(2) Date: Jan. 13, 2023

(87) PCT Pub. No.: WO2022/013303
PCT Pub. Date: Jan. 20, 2022

(65) Prior Publication Data
US 2023/0323272 A1 Oct. 12, 2023

(30) Foreign Application Priority Data

Jul. 16, 2020 (DE) .......................... 102020118898.6
Oct. 5, 2020 (DE) .......................... 102020126038.5

(51) Int. Cl.
*C12M 1/00* (2006.01)
*C12M 1/12* (2006.01)
(52) U.S. Cl.
CPC ............ *C12M 41/14* (2013.01); *C12M 23/28* (2013.01); *C12M 23/40* (2013.01); *C12M 37/04* (2013.01)
(58) Field of Classification Search
None
See application file for complete search history.

(56) References Cited

U.S. PATENT DOCUMENTS 4,195,131 A * 3/1980 Papas ..................... C12M 23/10
435/303.1
7,682,823 B1 3/2010 Runyon
(Continued)

FOREIGN PATENT DOCUMENTS

DE 102006004157 A1 8/2007
DE 102010012790 A1 9/2011
(Continued)

OTHER PUBLICATIONS

International Search Report for PCT/EP2021/069642 (Nov. 5, 2021).
(Continued)

*Primary Examiner* — Holly Kipouros
(74) *Attorney, Agent, or Firm* — Merchant Gould P.C.

(57) ABSTRACT

A device for providing a sterile environment for the incubation of cell cultures is proposed, comprising a warming chamber with heating elements, sensors for temperature, humidity and CO2, and a gas supply providing a gas connection in the interior. The device also has a cultivation tank located in the warming chamber. This has a sealable passage for each sensor, and also a sealable gas inlet and outlet that couples to the gas connection inside the warming chamber. The sensors of the warming chamber are arranged to fit into respective passages of the cultivation vessel. The device also has a water reservoir arranged in the cultivation tank. The three elements of the warming chamber, the cultivation container and the water reservoir can be sterilized separately using the optimal method for each. Since the sensors are not part of the cultivation container, the latter can also be decontaminated by high temperatures. The sterilized warming chamber ensures that the cell cultures in the cultivation container cannot be contaminated from the outside, nor can they cause contamination in the laboratory.

13 Claims, 4 Drawing Sheets

(56)     References Cited

U.S. PATENT DOCUMENTS

Figure 1:
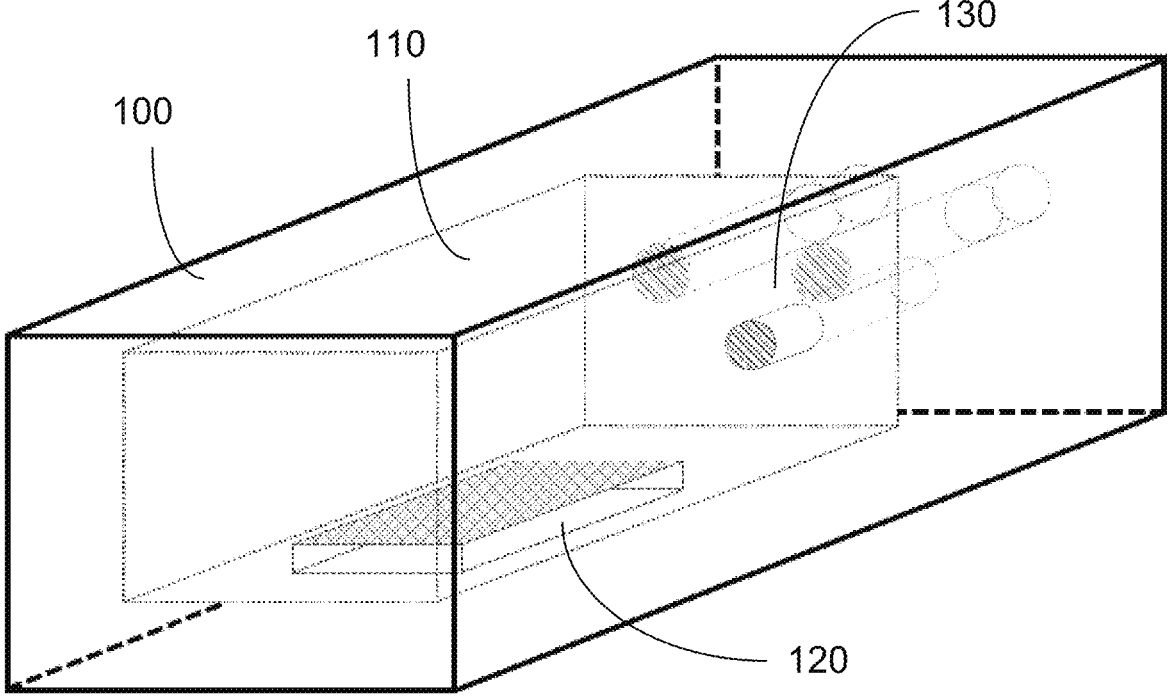

|  |  |  |  |  |
|---|---|---|---|---|
| 8,323,957 | B2 * | 12/2012 | Bartsch ................. | C12M 37/02 |
|  |  |  |  | 435/325 |
| 2005/0248836 | A1 * | 11/2005 | Tsuchiya .............. | G02B 21/362 |
|  |  |  |  | 359/368 |
| 2014/0158223 | A1 * | 6/2014 | Rothenberg .......... | C12M 23/46 |
|  |  |  |  | 137/343 |
| 2018/0104697 | A1 | 4/2018 | Butler et al. |  |
| 2018/0105787 | A1 | 4/2018 | Hardin |  |

FOREIGN PATENT DOCUMENTS

| DE | 102014106877 | A1 | 11/2015 |
|---|---|---|---|
| DE | 102017104508 | B3 | 3/2018 |
| EP | 0808657 | A2 | 11/1997 |
| EP | 1403363 | A1 | 3/2004 |
| EP | 1552888 | A2 | 7/2005 |
| EP | 2873724 | A1 | 5/2015 |
| EP | 2330181 | B1 | 11/2018 |
| WO | 2011/130865 | A2 | 10/2011 |
| WO | 2015/172882 | A1 | 11/2015 |

OTHER PUBLICATIONS

Biospherix, ProOx C21 Compact O2 CO2 Subchamber Controller,"D3-BioSpherix, ProOx C21 Compact O2 CO2 Subchamber Controller" Cell-Research-Literature_ProOx-C21.pdf.

* cited by examiner

410

420

120

DEVICE FOR ENSURING A STERILE ENVIRONMENT FOR INCUBATING CELL CULTURES

CROSS-REFERENCE TO RELATED APPLICATION(S)

This application is a National Stage Application of PCT/EP2021/069642, filed 14 Jul. 2021, which claims benefit of German Application Nos. 10 2020 118 898.6, filed 16 Jul. 2020, and 10, 2020 126 038.5, filed 5 Oct. 2020, and which applications are incorporated herein by reference. To the extent appropriate, a claim of priority is made to each of the above disclosed applications.

FIELD OF THE INVENTION

The invention relates to a device for ensuring a sterile environment for the incubation of cell cultures. Such devices are mainly used for the cultivation of cell cultures, mainly for medical and research purposes, where the sterility of all elements coming into contact with the cell cultures and the avoidance of any contamination of these cell cultures are of primary importance.

The invention of gene scissors (known as CRISP/CAS) has opened up the possibility of targeted modification of genetic material. Against this background, various research groups are already developing new cell-therapeutic therapies based on the manipulation of genetic material. In the field of human medical therapies, this will involve personalized medicine in Which patient material (i.e. living cells of a patient) is incubated in cell cultures before and after genetic manipulation. In order to strictly avoid contamination of this patient material, devices are needed to safely ensure a sterile environment for these cell cultures during the incubation phase.

STATE OF THE ART

Cell cultures are cultivated in incubators, inside which a selectable, constant temperature (usually 37° C.), an adjustable $CO_2$ concentration (e.g. 5%), and a high relative humidity should prevail. Thus, ideal growth conditions are provided in an incubator for any type of cells, i.e. for both desirable and undesirable cultures.

A particularly critical component in an incubator is the water supply. Basically, the water in the incubator has the task of ensuring a relatively high humidity of close to 100% so that the aqueous nutrient medium in which the cells of the cell culture are located does not evaporate or evaporates only very little. In order to prevent the growth of cell biological contaminants in the water reservoir, substances toxic to protozoa are typically added to the water.

Two problems arise from the above: First, contamination can be introduced with the water, which then multiplies in the incubator, even if a toxic substance is added to the water itself. Secondly, the combination of the relatively high humidity and the optimum temperature for cell growth stimulates any contamination that may be present to explosive growth, which is amplified many times over if the humidity condenses in the incubator.

In practice, the ideal growth conditions in the incubator result not only in the multiplication of patient cells, but also in the unintentional introduction of foreign cells, so-called impurities or contaminations. This can lead to contamination of the actual cell culture, the patient material, with the result that the patient material becomes unusable for therapy and, in the worst case, the patient dies as a result of the contamination.

With the aim of reducing contamination of the incubator by foreign cells, the interior of conventional incubators must be sterilized at regular intervals (de-contamination). For this purpose, the interior of the incubator is brought to temperatures close to 200° C. for a period of up to several hours. In this way, the population of cells present there is strongly decimated, but not completely extinguished. A reduction of the contamination by a factor of a thousand, for example, is common.

Another approach to reduce the risk of contamination is to place the samples in a separate, sealed container. This container is usually fitted with a gas-permeable membrane so that gas and moisture exchange with the atmosphere in the incubator is provided. The membrane itself is usually designed as a sterile filter, which largely minimizes the penetration of biological contaminants into the interior of the container. However, such containers do not prevent contamination within the incubator itself, and especially not on the outer surface of such a container. In particular, contamination can be deposited preferentially on the outer surface of the sterile filter of such a container, so that a carry-over of this contamination into the interior of the container cannot be ruled out.

In order to monitor or regulate parameters such as temperature or $CO_2$ concentration in the incubator, it is necessary to place sensors in its interior. However, many of these sensors are sensitive to high temperatures, e.g. the usual $CO_2$ sensors do not tolerate temperatures above 160° C. For this reason, decontamination of an incubator involves effort, as at least some of the sensors must be removed from the incubator beforehand. In addition, although these sensors cannot be decontaminated themselves, they must still be reinstalled in the interior of the incubator, which at least partially negates the effect of decontaminating it.

For many current applications in cell biology and medicine and especially for possible future applications, for example in the therapy of genetic diseases (e.g. tumors, leukemia or hereditary diseases), a completely sterile environment in the incubator is essential.

From the publication WO 2015/172882 A1, a system is known which is intended to increase safety in the laboratory by means of mutually self-sufficient mini-incubators, each designed for only one sample carrier, and in particular to prevent confusion and possible contamination of the samples. However, this system cannot guarantee complete sterility.

The publication WO 2011/130865 A2 describes an essentially conventionally designed incubator in which, in order to prevent contamination of the samples, it is intended to carry out as many treatment steps as possible within the incubator by machine, without human involvement. Special devices such as robotic arms are provided for this purpose. However, complete sterility cannot be guaranteed even in this case.

OBJECT OF THE INVENTION

The object of the invention is to provide a device that allows improvement of sterility in the incubation of cell cultures.

SOLUTION

This object is achieved by the subject-matters of the independent claims. Advantageous further embodiments of the objects of the independent claims are indicated in the sub-claims. The wording of all claims is hereby made the content of this description by reference.

The use of the singular is not intended to exclude the plural, which is also to apply in the reverse sense, unless otherwise disclosed.

To achieve this object, a device for ensuring a sterile environment for incubation of cell cultures is proposed. The device has a sealable and/or sealed warming chamber, which has at least one heating element. The warming chamber has sensors for temperature and/or humidity and/or CO2 and at least one connection for a gas supply on the outside. The connection is connected to a line which provides a gas connection in the interior of the warming chamber. The gas supply is typically CO2, but other gases may be provided for special cell cultures. The device also has a sealable and/or sealed cultivation container for holding the cell cultures, located in the warming chamber. The cultivation container does not have its own heating system. The cultivation container has a sealable passage for each of said sensors, which is in communication with the atmosphere in the cultivation container. The cultivation container also has at least one sealable gas inlet and/or outlet that can be coupled to the at least one gas connection in the interior of the warming chamber. The sensors of the warming chamber are arranged to be introduced into the respective sealable passages of the warming chamber when the cultivation container is inserted into the warming chamber. In this way, the sensors of the warming chamber can provide measurement data on the conditions in the cultivation container. The device further has a water reservoir arranged in the cultivation tank.

With this device, a considerable improvement in the sterilization situation during the incubation of cell cultures can be achieved, as the three elements of the warming chamber, cultivation container and water reservoir can be sterilized separately from one another using the optimum process for each. Since the sensors are not located in the cultivation container, the latter can be decontaminated, for example, by high temperatures (e.g. above 200° C.) if required. The sterilized warming chamber ensures that the cell cultures in the cultivation container cannot be contaminated from the outside or cause contamination in the laboratory.

The sealable gas inlet and/or outlet, which can be coupled to the gas port provided inside the warming chamber, enables the maintenance of optimal conditions in the cultivation vessel. These conditions can be controlled by means of sensors that fit into the sealable diffuser(s).

Possible contamination of the cell cultures in the cultivation container by the sensors can be prevented by covering each of said sensors of the warming chamber with a sterile filter.

Likewise, contamination by the gas supply can be avoided by the fact that the at least one connection of the warming chamber for a gas supply, the line connected thereto or the gas connection connected via this line and provided in the interior of the warming chamber has a sterile filter.

For inserting the cultivation container into the warming chamber, it is advantageous if the warming chamber has a tightly closing lid or door, wherein the opening of the lid or door has a cross-section that is larger than a width of the cultivation container.

Contamination by the sensors can also be prevented by ensuring that each sealable passage on the cultivation container has a sterile filter. This design is particularly preferred.

It can be used as an alternative to sterile filters directly on the sensors of the warming chamber or as a supplement to them.

Contamination by the gas supply can preferably be prevented by the at least one sealable gas inlet and/or outlet on the cultivation vessel having a sterile filter. This in turn can be used either as an alternative to sterile filters directly at the gas connection of the warming chamber or as a supplement thereto.

To ensure that the cultivation container has been sterilized before use, it is advantageous if the cultivation container is a disposable element. This can already be manufactured under sterile or clean room conditions.

The introduction of the sample carrier(s) with the cell cultures is facilitated if the cultivation container has a tightly closing lid or door.

It is particularly advantageous if the water reservoir is covered with a semi-permeable membrane. This membrane should be impermeable to water but allow water vapor to pass through. Nonwovens made of high-density polyethylene (PE-HD), for example, have proven excellent for this purpose. In this way, the water can already be added when the water reservoir is made.

Premature evaporation of the water from the water reservoir can be prevented if the semi-permeable membrane of the water reservoir is sealed before use with a film that is impermeable to water and water vapor, e.g. with a plastic film, which is removed for use.

Possible contamination of the cell cultures via the water reservoir becomes particularly unlikely if the water reservoir contains sterile ultrapure water.

The sterility of the water reservoir can be particularly well ensured if the water reservoir is a disposable element.

The incubation conditions in the cultivation tank can be set particularly optimally if a control and/or regulation system is present which is capable of influencing the conditions in the cultivation tank on the basis of data from the sensors of the warming chamber. The data of the temperature sensor are used to control and/or regulate the heating elements of the warming chamber and the data of the CO2 sensor are used to control and/or regulate the at least one gas supply. The data of the humidity sensor are used to output warning messages, which can prompt the user, for example, to renew the water reservoir if the humidity reaches a value that is too low.

The problem is further solved by a sealed and/or sealable cultivation container for holding cell cultures. The cultivation container has at least one sealable passage for a sensor which is in communication with the atmosphere in the cultivation container. Further, the cultivation container has at least one sealable gas inlet and/or outlet that is couplable to a gas port. Finally, a position for a water reservoir is located inside the cultivation container.

Such a cultivation container can be easily decontaminated, and/or even manufactured under sterile conditions. Contamination-sensitive samples can thus be placed in such a cultivation container and are then specially protected for the entire cultivation process. The cultivation container can then be placed in a warming chamber as described earlier. The sealable gas inlet and/or outlet, which can be coupled to the gas connection provided inside the warming chamber, makes it possible to maintain optimum conditions in the cultivation container. These can be controlled by means of sensors that fit into the sealable passage(s).

This cultivation container can thus be used in a device as described above.

Further details and features result from the following description of preferred embodiment examples in connection with the figures. The respective features can be implemented individually or in combination with one another. The possibilities of solving the problem are not limited to the embodiment examples. For example, range specifications always include all—not mentioned—intermediate values and all conceivable subintervals.

Figure 2:
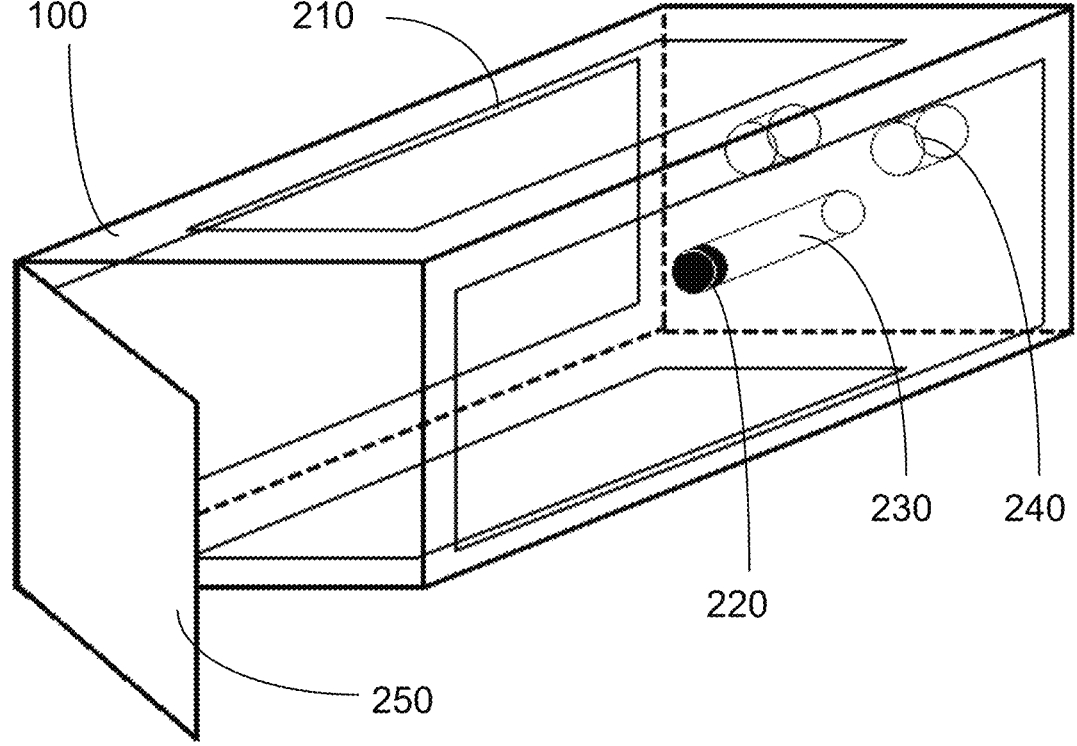
Figure 3:
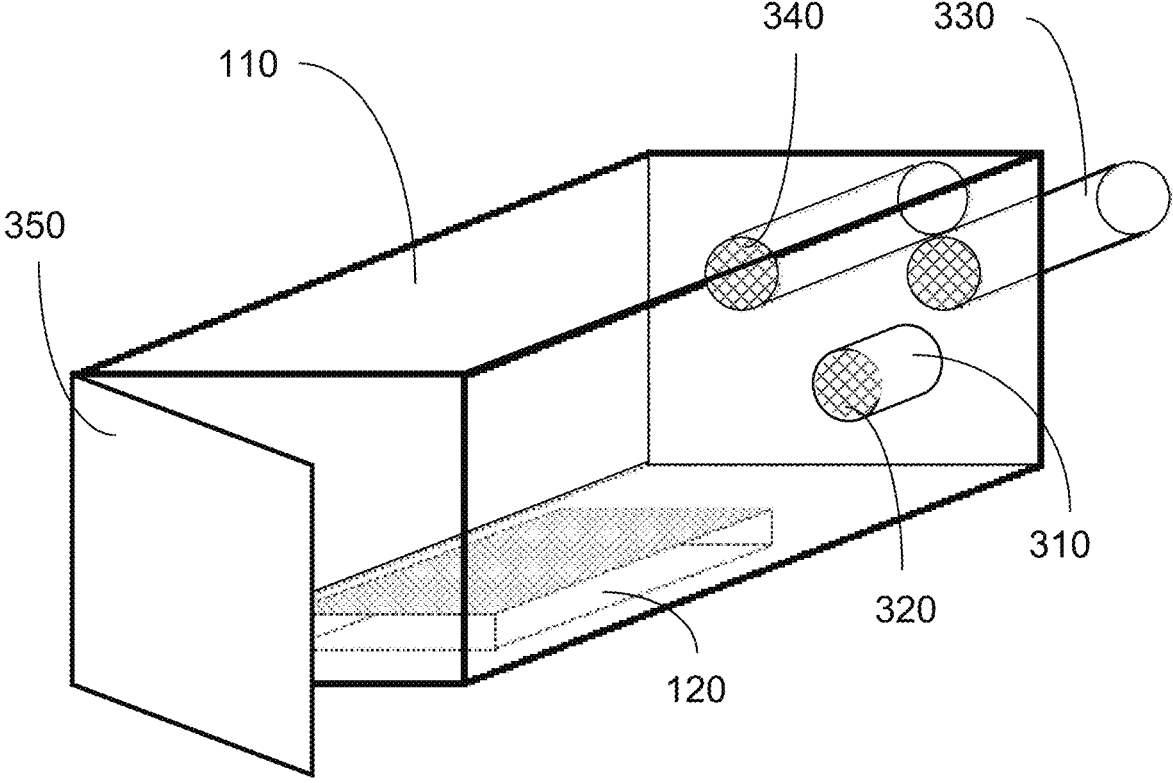
Figure 4:
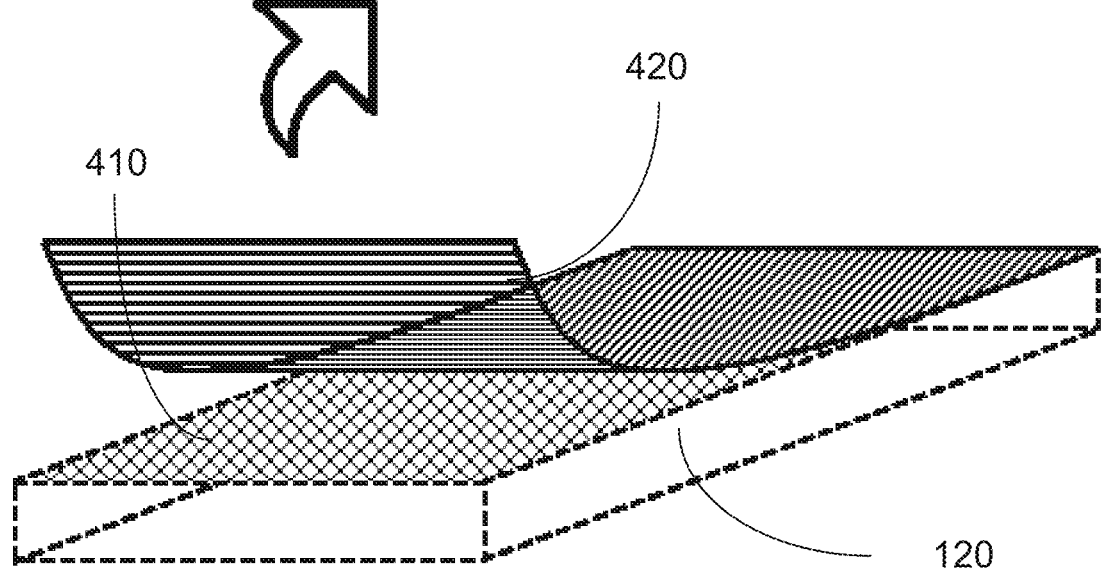

An example of an embodiment is shown schematically in the figures. Identical reference numerals in the individual figures denote identical or functionally identical elements or elements that correspond to one another in terms of their functions. In detail:

FIG. 1 a schematic overall representation of a device according to the invention;

FIG. 2 a schematic representation of a warming chamber of a device according to the invention;

FIG. 3 a schematic representation of a cultivation container of a device according to the invention; and FIG. 4 a schematic representation of a water reservoir of a device according to the invention.

FIG. 1 shows a device for ensuring a sterile environment for the incubation of cell cultures in overall view, so that the arrangement of the three main components in relation to one another can be seen. The warming chamber 100 is the outer element and, in normal operation, contains the cultivation container 110, which can be of different sizes depending on the cultures to be incubated. Preference is given to a design in which the cultivation container can accommodate a sample carrier, e.g. a microplate or a Petri dish. However, larger designs are of course also possible.

Inside the cultivation container, the water reservoir 120 is arranged. In the selected embodiment, connections or connecting elements 130 are arranged behind the cultivation container, which connect the cultivation container 110 to the warming chamber 100. These connections or connecting elements are described in more detail below in correlation with FIGS. 2 and 3.

FIG. 2 shows the warming chamber 100. This forms an outer shell that ensures the desired temperature. For this purpose, the warming chamber contains heating elements 210. The required sensors, e.g. for temperature, relative humidity or CO2 content, are also located in the warming chamber 100.

In FIG. 2, only the CO2 sensor 220 is shown for clarity. This is attached to a holder 230, which positions the sensor so that it is in the correct place when the cultivation container is inserted. Furthermore, at least one connection for a gas supply is provided. This port is connected to a conduit that provides a gas port 240 inside the warming chamber. Preferably, two such gas ports are provided, one of which provides a CO2 supply, for example, and the other of which provides a means for gas extraction.

Preferably, a door 250 is provided opposite the sensors and gas connections, which is designed to be gas-tight. Alternatively, for example, a removable lid or the like may be provided. The opening of the lid or door 250 should have a cross-section large enough to allow the cultivation container 110 to be inserted without difficulty.

To avoid contamination of the laboratory environment by bringing the warming chamber 100 into the laboratory, it is advantageous if the warming chamber is cleaned and placed in a package in which it can be sterilized before being brought into the laboratory. The packaging consists at least in part of a semi-permeable membrane that is gas-permeable but sufficiently fine-pored so that germs cannot pass through. Sterilization can then be carried out, for example, in a known manner by gassing with ethylene oxide.

FIG. 3 shows the cultivation container 110, which is inserted into the warming chamber and can be removed therefrom. The cultivation container has at least one sealable passage 310 for the sensors, which is in communication with the atmosphere in the cultivation container. This passage 310 is preferably covered on its inner side by a sterile filter 320, so that the cultivation container is protected against contamination from the outside. The warming chamber sensors are arranged to be inserted into the respective sealable passages of the cultivation container 110 when the cultivation container 110 is inserted into the warming chamber. As a result, they can provide data about conditions inside the cultivation container 110. The cultivation container also includes at least one sealable gas inlet and/or outlet 330 adapted to the at least one gas port in the interior of the warming chamber. Each of these gas inlets and/or outlets preferably has a sterile filter 340, so that the cultivation container 110 is protected against contamination from the outside, but also so that contamination from the cultivation container into the environment cannot occur. This may be necessary, for example, if infectious material is present in the cell culture. Preferably, a gas inlet and a gas outlet are provided in each case, which makes it easier to implement a gas exchange inside the cultivation container.

Furthermore, the cultivation container 110 has an opening through which, for example, sample carriers with cell cultures can be inserted into or removed from the cultivation container. This opening can be closed by means of a lid or a door 350. The closure by the lid or door 350 should be such that the cultivation container 110 is sealed gas-tight against the environment. Inside the cultivation container, it is further provided to accommodate a water reservoir 120.

In order to achieve the goal of ensuring a sterile environment for the incubation of cell cultures, it is provided that the cultivation container 110 is cleaned and sterilized prior to its use. In this regard, it is advantageous if the cultivation container 110 is disposable. The elements that are particularly critical for contamination, namely the passages 310 for the sensors, the gas inlets or outlets 330 and the associated sterile filters 320, 340 are part of the cultivation container. They are therefore included in the delivery, sterilized and also disposed of.

It also makes sense to provide special packaging for sterilization of the cultivation container 110, e.g. with a semi-permeable membrane. Various methods can be used for sterilization, e.g. gamma irradiation or gassing with ethylene oxide, or thermal methods.

For use of the cultivation container 110 in a cleanroom environment, it is also advantageous if the entire production of the cultivation container, including the sterile packaging, itself takes place in a cleanroom. The finished component (i.e., cultivation container 110 in the sterile packaging) can then still be provided with a cleanroom-compatible outer packaging (e.g., plastic bag).

In FIG. 4, a water reservoir 120 is schematically shown as a further component of the device according to the invention. In reality, this does not necessarily have to be cuboidal. A cylindrical or bubble-shaped design is also conceivable, for example. The water reservoir 120 preferably has a semi-permeable membrane 410, e.g. a Tyvek film or the like, on at least part of its surface. The semipermeable membrane allows gaseous water vapor to escape from the water reservoir to the atmosphere in the cultivation vessel, but prevents liquid water from leaking from the water reservoir.

Before the water reservoir is inserted into the cultivation container, the semipermeable membrane is preferably sealed by a film 420, e.g. a water- and gas-tight plastic film. The arrow in FIG. 4 indicates the removal of this sealing film 420 before insertion of the water reservoir.

It is particularly advantageous if the water reservoir 120 is designed to be inserted separately, as a disposable reservoir, into the cultivation container 110. In this case, the water reservoir 120 can already be filled with water during manufacture. Preferably, sterile ultrapure water is used.

In order to achieve the goal of providing a sterile environment for incubation, it is advantageous if the water reservoir 120 is externally sterilized prior to its use. For this purpose, the water reservoir can be placed in a package for sterilization, for example in a package with a semi-permeable membrane, as can the other components warming chamber 100 and cultivation container 110. Different methods can be used for sterilization, e.g. gamma irradiation or gassing with ethylene oxide.

For use of the water reservoir 120 in a clean room environment, it is also advantageous if the entire production of the water reservoir, including the water and the sterile packaging, takes place in a clean room and the entire component (i.e. water reservoir 120, water, water vapor permeable membrane 410, seal 420 and sterile packaging) is packaged once again in a clean room suitable container (e.g. plastic bag).

The device described above offers the following advantages over the prior art:

Since the gas inlet of the cultivation container is adapted to the warming chamber in such a way that there is no gas exchange between the warming chamber and the cultivation container, contamination of the sterile filter from the area of the warming chamber is not possible. The gas inlet or outlet only allows gas to pass from the gas connection to the cultivation tank.

Similarly, the gas outlet of the cultivation container is adapted to the warming chamber in such a way that gas exchange between the cultivation container and the warming chamber is prevented. In this way, contamination of the warming chamber from the area of the cultivation container is not possible.

Furthermore, the device according to the invention offers the advantage that the sensors are located outside the cultivation container and thus cannot be contaminated by the samples in the cultivation container, since they are separated from it by a sterile filter.

Furthermore, the use of a sterilized cultivation container prevents contamination of samples. This is especially true if the cultivation container is a sterilized disposable article.

The use of ultrapure water, which is introduced into the sterilized cultivation container in a sterilized disposable reservoir, also rules out contamination by the water introduced. This risk also does not exist in the event that the relative humidity is so high that water condenses in the cultivation container, as all components have been sterilized before use.

Glossary

Incubator

An incubator is a device used in biology to create and maintain controlled outdoor conditions for various development and growth processes. It is used to create and maintain a microclimate with tightly controlled humidity and temperature conditions. An incubator is equipped with a timer and a temperature controller and, under certain circumstances, a setting for the regulation of the supplied fresh air. The set temperature is adjusted to the optimum temperature of the microorganisms to be incubated. CO2 incubators are used for the cultivation of animal cells. (According to de.wikipedia.org/wiki/Incubator_(Biology)).

Microplate

A microwell plate (or microplate) is a multiple sample carrier. The usually rectangular microplates are usually made of plastic, for very special applications also of glass. They contain between 6 (2×3) and 1536 (32×48) wells isolated from each other in rows and columns. The exact dimensions (length×width×height) are 127.76×85.48×14.35 mm according to ANSI standard on the recommendation of the Society for Biomolecular Screening (SBS). Microplates are used for a wide variety of microbiological operations. Typical applications are cell cultivation or screening of technical bioreactions. Due to the large number of wells and the use of identical types, microplates are suitable for parallel cultivation and testing of a large number of different samples. Due to the standardized size, almost all operations can be automated with suitable robots. (According to de.wikipedia.org/wiki/Microtiterplate).

Sample Carriers

Microbiological samples or cell cultures are stored in containers, which are referred to here as sample carriers. Depending on the type of samples, these can be a wide variety of containers. Typically, however, Petri dishes or microplates are used, sometimes also Erlenmeyer flasks or similar. Multiple sample carriers, for example microplates, are also referred to as sample carrier systems.

Sterile Filter

In sterile filtration, microorganisms are separated from the material to be sterilized by filtration. Membranes with a pore diameter of 0.1 to 0.22 $\mu$m are usually used as filters. Sterile filtration is often used to sterilize heat-sensitive solutions, for example tissue culture solutions containing serum. Main applications are sterile filtration of aqueous solutions, heat sensitive nutrient solutions, vitamin solutions, sera, viral vaccines, plasma fractions and protein solutions. (According to https://de.wikipedia.org/wiki/Sterilisation #Sterilfiltration).

REFERENCE SIGNS

- 100 Warming chamber
- 110 Cultivation container
- 120 Water reservoir
- 130 Connections or connecting elements
- 210 Heating element
- 220 CO2 sensor
- 230 Holder for sensor
- 240 Gas connection
- 250 Door of the warming chamber
- 310 Passage for sensor
- 320 Sterile filter for sensor
- 330 Gas inlet or outlet
- 340 Sterile filter for gas inlet or outlet
- 350 Door of cultivation vessel
- 410 Semipermeable membrane
- 420 Film

CITED LITERATURE

WO 2015/172882 A1
WO 2011/130865 A2

The invention claimed is:

1. A device for providing a sterile environment for the incubation of cell cultures comprising:

a sealed warming chamber;

wherein the warming chamber comprises at least one heating element;

wherein the warming chamber comprises sensors for temperature and/or humidity and/or $CO_2$;

wherein the warming chamber has at least one connection for a gas supply on an exterior of the warming chamber, wherein the connection is connected to a tube that provides a gas connection in the interior of the warming chamber;

a sealed cultivation container for holding the cell cultures;

wherein the cultivation container is located in the warming chamber;

wherein the cultivation container has a sealable passage in communication with the atmosphere in the cultivation container for each of said sensors of the warming chamber;

wherein the cultivation container comprises at least one sealable gas inlet and/or outlet that is couplable to the at least one connection for a gas supply in the interior of the warming chamber;

wherein the sensors of the warming chamber are arranged to be introduced into the sealable passages of the cultivation container upon insertion of the cultivation container into the warming chamber; and a water reservoir;

wherein the water reservoir is arranged in the cultivation container.

2. The device according to claim 1, wherein each of said sensors of the warming chamber is covered by a sterile filter.

3. The device according to claim 1, wherein the at least one connection of the warming chamber for a gas supply, the tube connected thereto or the gas connection connected via this tube and provided in the interior of the warming chamber comprises a sterile filter.

4. The device according to claim 1, wherein the warming chamber has a tightly closing lid or door having an opening;

the opening of the lid or door has a cross-section that is larger than a width of the cultivation container.

5. The device according to claim 1, wherein each sealable passage on the cultivation container comprises a sterile filter.

6. The device according to claim 1, wherein the at least one sealable gas inlet and/or outlet on the cultivation container comprises a sterile filter.

7. The device according to claim 1, wherein the cultivation container is a disposable element.

8. The device according to claim 1, wherein the cultivation container has a tightly closing lid or a tightly closing door.

9. The device according to claim 1, wherein the water reservoir is covered with a semi-permeable membrane.

10. The device according to claim 9, wherein the semi-permeable membrane of the water reservoir is sealed prior to use with a film impermeable to water and water vapor, which is removed for use.

11. The device according to claim 1, wherein the water reservoir contains sterile ultrapure water.

12. The device according to claim 1, wherein the water reservoir is a disposable element.

13. The device according to claim 1, comprising:

a control and/or regulation system is provided;

wherein the control and/or regulation system is capable of influencing conditions in the cultivation container based on data from the sensors of the warming chamber;

wherein the temperature sensor data is used to control and/or regulate the at least one heating element of the warming chamber; and/or wherein the data of the $CO_2$ sensor serves to control and/or regulate the at least one gas supply; and/or wherein the data of the humidity sensor serve to output warning messages.

* * * * *